United States Patent [19]

Ozawa et al.

[11] Patent Number: 5,690,893
[45] Date of Patent: Nov. 25, 1997

[54] ANALYZER HAVING SENSOR WITH MEMORY DEVICE

[75] Inventors: Satoshi Ozawa, Musashino; Takafumi Kikuchi, Kokubunji; Yoshiki Murakami, Kawasaki; Masaaki Nakai, Tokorozawa; Koutarou Yamashita; Toshiko Fujii, both of Kokubunji; Yuji Miyahara, Kodaira; Yoshio Watanabe, Kokubunji, all of Japan

[73] Assignee: Hitachi, Ltd., Tokyo, Japan

[21] Appl. No.: 461,160

[22] Filed: Jun. 5, 1995

[30] Foreign Application Priority Data

Jun. 10, 1994 [JP] Japan ................... 6-129244

[51] Int. Cl.[6] ............................... G01N 27/333
[52] U.S. Cl. ..................... 422/67; 422/63; 422/81; 422/82.03; 436/43; 436/50; 436/180; 364/497
[58] Field of Search ..................... 422/67, 82.01, 422/82.03, 105, 119, 62; 436/43, 50, 55; 380/25; 204/403, 406; 364/497

[56] References Cited

U.S. PATENT DOCUMENTS

| | | |
|---|---|---|
| 4,362,935 | 12/1982 | Clark, III ............... 378/48 |
| 4,580,721 | 4/1986 | Coffee et al. ............ 239/3 |
| 4,686,479 | 8/1987 | Young et al. ............ 324/439 |
| 4,695,430 | 9/1987 | Coville et al. .......... 422/65 |
| 4,940,945 | 7/1990 | Littlejohn et al. ....... 324/438 |
| 4,975,647 | 12/1990 | Downer et al. .......... 324/425 |
| 5,053,199 | 10/1991 | Keiser et al. ........... 422/68.1 |
| 5,108,564 | 4/1992 | Szuminsky et al. ....... 204/153.12 |
| 5,281,395 | 1/1994 | Markart et al. ......... 422/82.05 |
| 5,357,953 | 10/1994 | Merrick et al. ......... 128/633 |
| 5,366,609 | 11/1994 | White et al. ........... 204/403 |

*Primary Examiner*—Long V. Le
*Attorney, Agent, or Firm*—Antonelli, Terry, Stout & Kraus, LLP.

[57] ABSTRACT

An analyzer includes an exchangeable and consumable element such as a sensor, column or reagent the characteristic of which specifies an analyzing condition. The element is provided with a non-volatile semiconductor memory which holds an analyzing condition adapted for the element as data. When the element is mounted on an analyzer body, a controller of the analyzer reads the analyzing condition from the memory to update an analyzing condition inherently provided in the analyzer body. The result of analysis and/or operational history information of use of the element may be written into the memory with which the element is provided.

48 Claims, 6 Drawing Sheets

ANALYZER HAVING SENSOR WITH MEMORY DEVICE

BACKGROUND OF THE INVENTION

The present invention relates to an analyzer and is preferably applicable to, for example, an automatic blood analyzer or the like.

An analyzer such as an automatic blood analyzer may encounter the case where a need to change the analyzing condition of a sample (for example, temperature or reaction time) is generated when a new version of a sensor or reagent of the analyzer is employed (or the improvement in performance or change in specification of a sensor or reagent is made). The change of the analyzing condition has been made to an analyzer body through a manual input or by use of an information inputting medium such as a floppy disk.

Regarding an analyzer using various reagents, it is known that a reagent vessel is provided with a bar code representing the kind and the lot number of a reagent included in the vessel and the free-setting of reagent, a lot management, the management of effective term and so forth are made using the bar code information (see JP-A-05-288756).

However, in the case of an automatic blood analyzing system involving a large number of inspection items and many kinds of sensors and reagents, there is a problem that the updating of analysis software stored in an analyzer body made for each improvement in performance or change in specification of an individual sensor or reagent is troublesome to a user and attention must be paid to the synchronization of the exchange of an old sensor or reagent for a new one with the updating of the analysis software.

Further, a user having some kinds of equipments among a series of analyzers consisting of plural kinds of equipments slightly different in function or analysis software must update information stored in an analyzer body by use of a manual input, a floppy disk or the like for each replaceable part and for each kind of equipment in accordance with the improvement in performance or change in specification of replaceable parts. This is very troublesome to the user and imposes a very large load on a service department of a manufacturer or the like which supports all such users.

SUMMARY OF THE INVENTION

The present invention concerns an analyzing system using a replaceable part such as a sensor, reagent or the like including a part which is consumed by operating an analyzer or a part which is exchangeable for the improvement in performance or the like. An object of the present invention is to make it possible in such a system to input a large amount of information inclusive of a new analyzing condition concerning the replaceable part to an analyzer body by use of simple means. The term of "replaceable part" used in the present specification means a part such as a sensor, column for chromatography, reagent or the like the characteristic of which defines an analyzing condition. For example, the sensor defines a start-up time. A floppy disk used exclusively for inputting data and information is not included by the term of "replaceable part".

The above object is attained by mounting a semiconductor memory such as a non-volatile memory on a replaceable part (consumable or exchangeable part) such as a sensor or reagent vessel used in form mounted on an analyzer body, storing information of an analyzing condition or the like in the semiconductor memory, and reading the information from the replaceable part by the analyzer so that the information of the analyzing condition or the like inherently provided in the analyzer is replaced or extended by the read information, as required.

The information stored in the semiconductor memory may include information for operating the analyzing system, an analyzing condition concerning a sensor or reagent including the memory carried thereby, the record of information on operational history (i.e., operational history information) of the analyzing system, the result of analysis, and so forth.

The semiconductor memory can be formed as a part unit so that the memory unit is detachably mounted on the sensor, reagent vessel or the like. Thereby, the memory unit can be recovered from the spent sensor, reagent vessel or the like for repeated use.

Before a replaceable part such as a sensor or reagent bearing a part of an analyzing function is offered to a user, a semiconductor memory is mounted on the replaceable part and a large amount of information inclusive of a new analyzing condition or the like is stored into the semiconductor memory (for each kind of equipment in the case where a plural kinds of equipments exist for an analyzer).

A processor or controller included in the body of an analyzer is programmed beforehand as follows. Namely, at the stage of time when the user mounts the offered replaceable part to the analyzer, the processor of the analyzer reads the information from the memory mounted on the replaceable part. When new information for operating the analyzer body is included in the read information, the processor replaces or extends information of an analyzing condition or the like provided in the analyzer by the read new information, as required.

With the above, it becomes possible for the user to cope with the improvement in performance or change in specification of a replaceable part by merely mounting a new replaceable part to the analyzer. In this case, it is not required that the user or a service department should be conscious of a distinction between a new sensor and an old sensor and the difference of one analyzer from the other. Namely, a large amount of information inclusive of a new analyzing condition concerning a consumable replaceable part bearing a part of an analyzing function can be inputted to an analyzer by simple means.

In the case where a non-volatile memory is used as the semiconductor memory, no power source is required for holding the information and hence there is no fear that the information is lost even if the replaceable part is transported or preserved in a state in which it is not mounted on the analyzer.

BRIEF DESCRIPTION OF THE DRAWINGS

The above and other objects and technical advantages of the present invention will be readily apparent from the following description of the preferred exemplary embodiments of the invention in conjunction with the accompanying drawings, in which.

DESCRIPTION OF THE PREFERRED EMBODIMENTS

The present invention will now be described by use of embodiments thereof.

[Embodiment 1]

Figure 1:
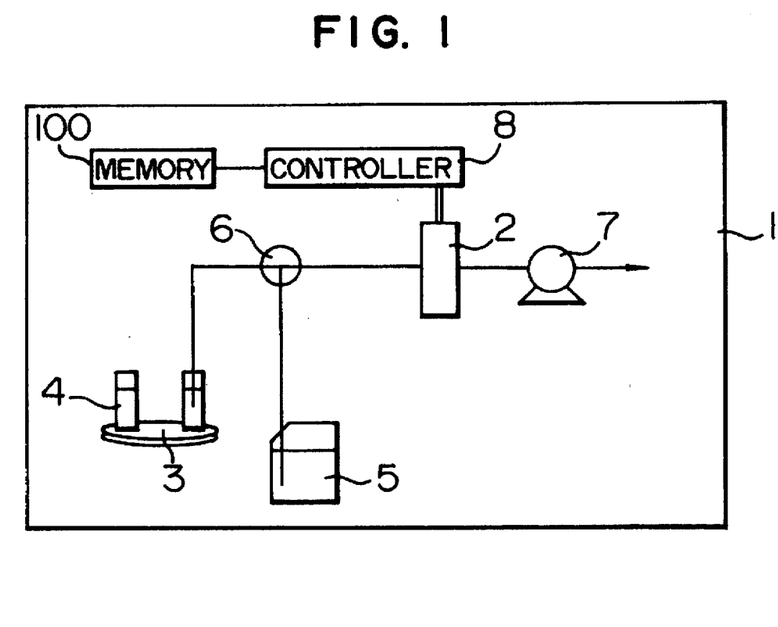
FIG. 1 is a diagram schematically showing the construction of an analyzer according to an embodiment of the present invention.

FIG. 1 is a diagram schematically showing the construction of an analyzing system or analyzer according to a first embodiment of the present invention.

A sensor 2 is mounted on an analyzer body 1. A sample in a sample vessel 4 is pipetted and diluted by a sampling mechanism 3. A part of the diluted sample and a reagent in a reagent vessel 5 are selected by an electromagnetic valve 6 and are alternately supplied to a passage 9 (see FIG. 2) in the sensor 2 by a solution feeding mechanism 7. Clinical Analyzer (Type 911) provided by Hitachi, Ltd. is applicable as the analyzer body 1. A signal corresponding to the concentration of a specified component included in each of the diluted sample and the reagent is outputted from the sensor 2 to a connector 12a by the action of a sensing member 10 provided in contact with the passage 9. A controller 8 comprising a processor controls the operation of each part of the analyzer. The controller 8 determines the concentration of the specified component in the sample on the basis of the detection signal, the concentration of the specified component included in the reagent, the magnifying factor of dilution, and so forth. The determined concentration of the specified component in the sample is displayed, outputted and stored. A preset measuring condition and a program necessary for operating the analyzer body 1 are held in a memory 100. The contents of the memory 100, particularly, the measuring condition are rewritable or extensible.

Figure 2:
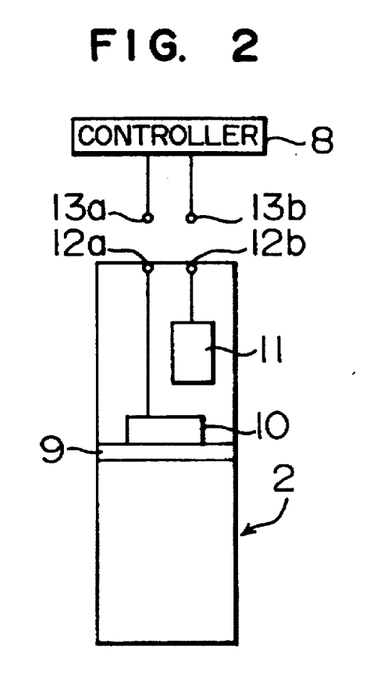
FIG. 2 is a diagram schematically showing the construction of a sensor-memory assembly in the embodiment shown in FIG. 1.

In general, the lifetime of the sensor 2 is short as compared with that of the analyzer body 1. In order to facilitate the exchange of a consumed sensor for a new sensor, the sensor is attachable to and detachable from the analyzer body 1. When the improvement in performance or change in specification of the sensor 2 is made after the analyzer body 1 has been offered to a user, there may be the case where it is desirable to change the analyzing condition of the offered analyzer body for coping with such improvement in performance or change in specification. In order to input such a large amount of unexpected new information to the analyzer body, the sensor 2 is provided with a non-volatile memory 11 incorporated therein, as shown in FIG. 2. A new sensor to be used under a new analyzing condition is delivered or consigned after a part or all of the new analyzing condition is stored into a non-volatile memory 11 of the new sensor at the time of manufacture.

Also, the controller 8 of the analyzer body is provided with a function of reading the contents of a non-volatile memory incorporated in each sensor at the time of start or at the time of parts exchange to displace or extend information of analyzing condition or the like in the memory 100, as required. The controller 8 comprises a microcomputer.

Figure 3A:
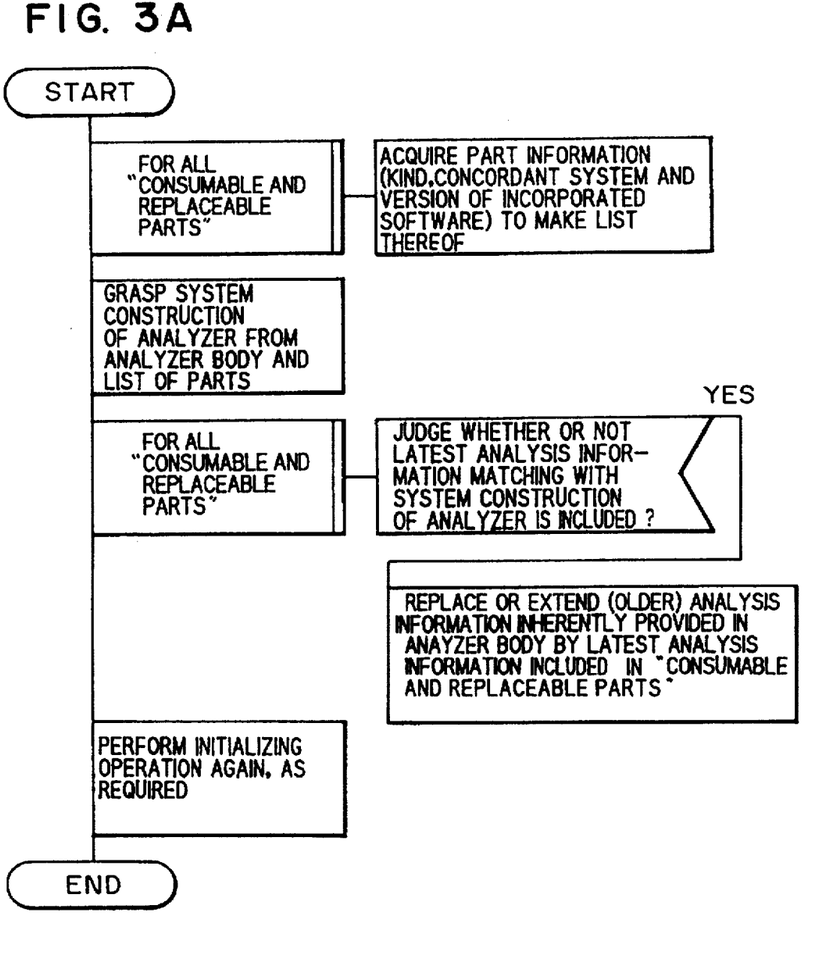
FIGS. 3A and 3B are flow charts showing the operation of the analyzer shown in FIG. 1.

When the analyzer body is started after the new sensor has been mounted on the analyzer body, the controller 8 acquires information for all replaceable parts inclusive of sensors on the kinds of the parts, concordant system, version of incorporated software to make a list thereof, as shown in FIG. 3A, so that the overall construction of the analyzer is grasped from the analyzer body and the part list. Further, the controller 8 makes the judgement of all parts as to whether or not the latest or newest analysis information or analyzing condition matching with the overall construction of the analyzer is stored in a memory attached to each part. In the case where there is the newest analysis information, analysis information inherently provided in the analyzer body is replaced or extended by the newest analysis information. Thus, the analyzer body reads a part or all of a new analyzing condition stored in the memory 11 of a new sensor, as required, for replacement or extension of information provided in the analyzer body. Thereby, a measurement under the new analyzing condition becomes possible. In the case where there is a part which has no newest analysis information in a memory 11 attached thereto, an analyzing condition beforehand provided in the memory 100 is used as an analyzing condition defined by that part.

Figure 3B:
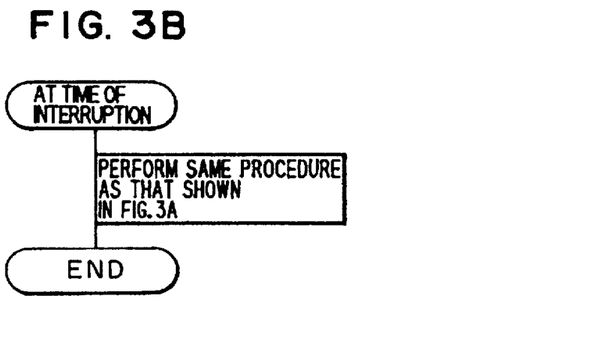

Also, the presence or absence of the exchange of a part such as a sensor is periodically monitored through an interruption processing by a timer, as shown in FIG. 3B. In the case where the exchange is found out, a processing similar to that mentioned above is performed. With such a construction, even in the case where the old sensor is exchanged for a new sensor in a state in which the analyzer has already been started, a new analyzing condition incorporated in the new sensor is acquired, thereby enabling a measurement under the new analyzing condition.

More specific explanation will now be made in conjunction with the case where an automatic blood analyzer is used as the analyzer body and an ion-selective electrode is used as the sensor.

At the initial stage, a start-up operation of about 30 minutes was required for the ion-selective electrode. The start-up operation is an operation until a measurement becomes possible after the mounting of the electrode to the analyzer body. During the start-up operation, the automatic blood analyzer body repeats an operation of feeding a reagent to the electrode. The significance of this operation includes to wait the electrode for being adapted to the reagent so that it is stabilized.

Thereafter, a time necessary for the start-up operation was reduced to about 15 minutes by the attainment of the stabilization of the electrode through the improvement of the electrode and in combination with the optimization of the start-up operation. In the present embodiment, a non-volatile memory is incorporated into an improved new sensor and a new software for performing the shortened and improved new start-up operation is stored in the non-volatile memory.

When the new sensor is mounted on the automatic blood analyzer, that is, when the connectors 13a and 13b on the controller 8 side are connected to the connectors 12a and 12b on the sensor assembly side, respectively, the automatic blood analyzer body reads the shortened and improved new start-up operation software through the connectors 12b and 13b from the non-volatile memory 11 of the new sensor, as mentioned above. Confirming that the read operation is a start-up operation which is newer than the previous start-up operation, the automatic blood analyzer body uses the new start-up operation in place of the old start-up operation stored in the memory 100. Thereby, a user can enjoy a merit that a time until the start of measurement can be reduced to a half. In updating the analyzing condition, the minimum operation of mounting the new sensor to the automatic blood analyzer body is only needed for the user side and it is not required at all that the user be conscious of the updating of the analyzing condition. Also, only the mere change of the kinds of sensors to be handled suffices on the supporting department side such as a manufacturer which supplies sensors to users.

Though the above explanation has been made supposing the case where the kind of the analyzers is one in number, there may be the case where analyzers belonging to the same system are offered as a series of plural kinds of equipments. In such a case, the effect of the present invention becomes more remarkable. Namely, a plurality of new softwares for performing new start-up operations corresponding to the individual kinds of equipments are stored in a memory attached to a new sensor together with markers or (symbols) which indicate the corresponding kinds of equipments.

When the new sensor is offered to a user and mounted on an automatic blood analyzer, an individual kind of equipment makes, on the basis of the above-mentioned markers, the judgement of whether or not a new software corresponding to its own kind of equipment exists in a memory attached to the new sensor. In the case where the new software exists, this new software or the shortened and improved start-up operation is used in place of the previous start-up operation in a manner similar to that mentioned above. In the case where all kinds of equipments possessed by the user correspond to the new software, the user can enjoy, for all kinds of equipments, a merit that a time until the start of measurement can be reduced to a half. In updating the analyzing condition, the minimum operation of mounting the new sensor to each automatic blood analyzer body is only needed for the user side and it is not required at all that the user be conscious of the updating of the analyzing condition for each kind of equipment. Also, on the supporting department side such as a manufacturer supplying sensors to users, anything to be coped with for each kind of equipment is not needed at all and only the mere change of the kinds of sensors to be handled suffices.

Though the present embodiment has been explained taking the shortening of the start-up operation time as an example of the new analyzing condition, the new analyzing condition is not limited to such an example. The optimum analyzing condition corresponding to any improvement in performance or change in specification of an electrode can be supplied to the automatic blood analyzer body very simply in a manner similar to that mentioned above. The analyzing condition concerning a sensor may include, for example, the kind and composition of used reagent (standard solution, diluent), pH, reaction time, agitation time, the pipetting amount of sample, the amount of diluent, the magnifying factor of dilution, the amount of solution introduced to the sensor, introducing time, introducing flow amount, introducing flow rate, temperature, pressure, measurement cycle time, measurement waiting time, data acquisition time, the number of times of data acquisition, applied voltage, applied current, input impedance, the kind of sensor, the lot number of sensor, the selectivity of sensor, correction factor, time-dependent response characteristic, sensitivity, analytical curve (or calibration curve), normal output range, warning condition, remeasuring condition, data processing algorithm, and so forth.

In the case where the data processing algorithm is stored in a non-volatile memory inside a sensor, the sensor for taking charge of the generation of data and the algorithm for processing the data are united. From the point of view of information processing, this corresponds to the capsulation of data and algorithm as an object. Accordingly, the present system can be regarded as being an object-oriented analyzing system.

Non-volatile semiconductor memories include mask ROM, EEPROM, flash EEPROM, FRAM and so forth. The EEPROM, flash EEPROM and FRAM capable of flexibly coping with the rewriting and/or addition of information can be preferably used in the present invention. The flash EEPROM or FRAM can be formed with a high density of integration since the number of transistors required for one cell is 1 (one) which is one half of that of the EEPROM.

In the present embodiment, a flash EEPROM is used. However, a FRAM may be used since it has a merit that the writing rate of the FRAM is high by about two ordors of magnitude as compared with that of the flash EEPROM and the tolerable number of times of rewriting is large by about three ordors of magnitude as compared with that of the flash EEPROM. In general, the above-mentioned non-volatile semiconductor memories can be preferably used in the present invention since they have the merits of small size, light weight, high degree of integration, low cost, and so forth. However, in the case where those merits are not required specifically, another semiconductor memory (for example, CMOS memory) may be used in combination with a backup power supply.

In general, since the non-volatile semiconductor memory has a plurality of address lines, the number of poles of the connector 12b becomes large if no countermeasure is taken. In order to avoid this problem, the non-volatile memory can be provided with a peripheral circuit which enables a processing of communication to the analyzer body. The communication system may be, for example, a half-duplex serial asynchronous communication system in order to simplify a hardware for communication, and there may be employed a protocol in which the sensor side continuously transmits data of 1024 bits for address designation and data request from the analyzer body. It is of course that another system can be used as the communication system or protocol in accordance with circumstances. Also, various wireless communication systems can be used in lieu of the wire communication system.

[Embodiment 2]

Figure 4A:
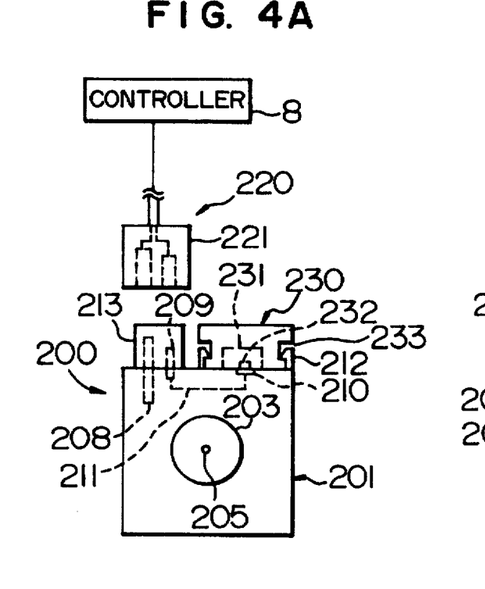
FIGS. 4A and 4B are a front view and a cross section schematically showing the construction of a sensor-memory assembly in another embodiment of the present invention.
Figure 4B:
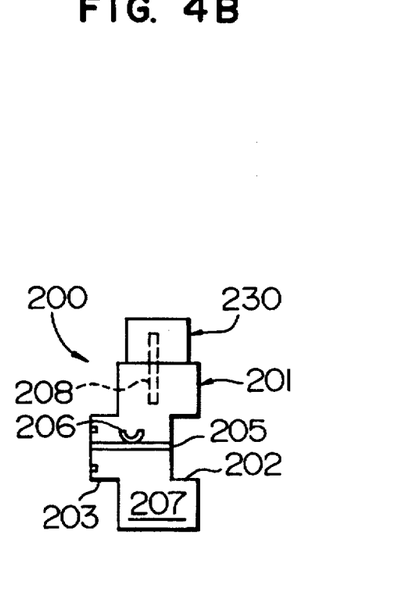

The foregoing explanation has been made in a simplified form in which the non-volatile memory is incorporated in the sensor directly. However, there may be employed an embodiment in which a member including a non-volatile memory is formed as a part unit so that this non-volatile memory unit is attachable to and detachable from a sensor. FIGS. 4A and 4B show the construction of an assembly 200 of sensor package and memory unit in such an embodiment.

The assembly 200 is composed of a sensor package 201 and a memory unit 230. The sensor package 201 is provided with a recessed portion 202 and a projected portion 203 for connection with other packages and has a passage 205 which extends passing through the center. The package 201 has therein a sensing member constituted by an electrode 206 arranged facing the passage 205 and is filled with a conductive material 207. The conductive material 207 electrically connects the sensing member of electrode 206 and a connector 208.

The sensor package 201 further includes connectors 209 and 210 and a line 211 for connecting the connectors 209 and 210. The connectors 209 and 210 and the line 211 are isolated from the conductive material 207 in a well known manner. The connector 209 is connected to a connector 220 on the controller 8 side. On the other hand, the connector 210 is electrically connected to a connector 232 of a memory 231 in contact therewith.

A retainer 212 is formed on the upper surface of the sensor package 201. A recessed portion 233 of the memory unit 230 is detachably engaged with the retainer 212. The manner of coupling of the sensor package 201 and the memory unit 230 is not limited specifically so long as the attachment and detachment of the sensor package and the memory unit are possible. For example, they can be coupled by a magnetic force or an adhesive. In this case too, the sensor package side and the memory unit side have their surfaces which are opposite to each other and provide means indispensable for detachably connecting the sensor package and the memory unit.

The sensor package 201 is detachably mounted on the analyzer body. In the present embodiment, the connectors 208 and 209 of the package 201 are connected to the connector 220 on the analyzer body side so that the package 201 and the analyzer body are connected through a mechanical coupling between the connector 220 of the analyzer body and the connectors 208 and 209 of the package 201 and between sleeves 213 and 221. It is of course that the manner of coupling of the package and the analyzer body is not limited to the shown example.

Figure 4C:
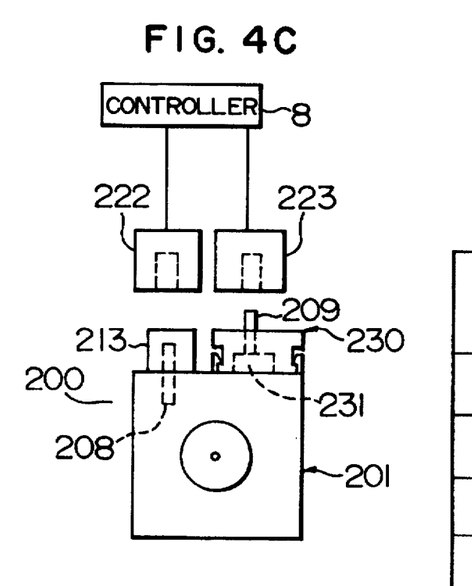
FIG. 4C is a front view schematically showing a modified example of the construction of a sensor-memory assembly.

The memory 231 is equivalent to the non-volatile semiconductor memory 11 shown in FIG. 2. As in a modified example shown in FIG. 4C, the connector 209 may be provided directly to the memory unit 230. In this case, the connectors 210 and 232 and the line 211 are omitted and two connectors 222 and 223 are provided on the controller side. The two connectors 222 and 223 may be united.

The above construction can be applied to all embodiments which will be explained in the following.

The construction according to the present embodiment provides the following effects. For example, in the case where a manufacturer recovers spent sensors, a non-volatile memory unit can be reused by removing the same from the spent sensor, thereby making it possible to reduce the manufacturing cost of the sensor. In the case where the non-volatile memory units are also employed in other kinds of apparatuses or equipments and are widely used as a de facto standard so that a recovering and recycling market is formed, it is possible to reuse a non-volatile memory unit obtained from the market.

Supposing such reuse, it is preferable that a operational history information storage area for storing the particulars of reuse is provided and that data, such as analyzing condition and analysis result, concerning analyzing system are stored in the remainder areas. In substance, the particulars of reuse of the non-volatile memory are successively recorded in the operational history information storage area in such a manner that the summary of the using condition in each use from the start of use to the end of use is stored as one record. The summary of the using condition includes, for example, the dates of start and end of use, the number of times of rewriting, a using product code (or the code of a product subjected to use of the memory), a user code, and so forth.

It is preferable that the programming is made so that the recording of the operational history information is automatically performed by the controller 8 of the analyzer body 1. For example, in the case where access to a non-volatile memory is made at the time of start-up or at the time of parts exchange and it is found out that the latest record of the operational history information is vacant or the using product code of the latest record is different from the product code of the analyzer body 1 itself, the controller 8 of the analyzer body 1 determines that the use of a part having this non-volatile memory incorporated therein is to be newly started in this analyzing system. In this case, the controller 8 ensures a new recording region in the operational history information storage area of the memory and writes the data of start of use, a using product code and a user code into the new recording region. It is of course that the provision of such a new record can be made by a manufacturer of parts when the non-volatile memory is incorporated into the part under consideration. This new record is made a record to be subjected to storage (or rewriting). In the case where the using product code of the latest record of the operational history information is the same as the product code of the analyzer body 1 itself, the controller 8 of the analyzer body 1 makes the judgement as a continued use and this latest record is made an object of storage (or rewriting) in that session as it is.

The controller 8 updates the number of times of rewriting recorded in the operational history information storage area of the memory attached to the sensor each time rewriting operation is performed. At the time of stop of the system, the controller 8 writes the date of end of use into the operational history information storage area.

By thus programming each analyzing system (and an initializing apparatus at the time of manufacture or reuse), it becomes possible to record the summary of the using condition in each use from the start of use to the end of use as an individual record in the operational history information storage area.

With the utilization of the operational history information, a user can grasp the previous using conditions of a non-volatile memory unit. For example, the actual number of times of rewriting and the tolerable number of times of rewriting inherent to that non-volatile memory can be utilized as information for judging whether or not the memory unit is to be subjected to reuse. Namely, the possibility of the life of the memory unit getting near the expiration can be preliminarily estimated by comparing the actual number of times of rewriting and the tolerable number of times of rewriting. On the other hand, storage areas other than the operational history information storage area are once subjected to erasion prior to each use and it can thereafter be used by writing any information into the storage areas in any format by a user. In the present embodiment, it is required that a specified format be defined so that the controller of the analyzer body can utilize information in the sensor.

[Embodiment 3]

Next, a third embodiment of the present invention will be explained. The construction of third present embodiment is substantially the same as to that of the first embodiment. The operation of the third embodiment is substantially similar to that of the first embodiment but different therefrom in that additional operations are performed so that a non-volatile memory 11 included in a sensor 2 is used not only for storing information of a new analyzing condition or the like but also for storing the operation record of the sensor.

Explanation will be made of a first additional operation or the estimation for the life of the sensor. An analyzer body operates so that an operation record parameter, i.e. information concerning operational history of sensor, providing a index of the life of the sensor acquired at the time of measurement or at the time of maintenance is properly stored into the non-volatile memory. In estimating the life, this operation record parameter is read from the non-volatile memory to analyze the tendency of change of the parameter value for the lapse of time or the number of samples subjected to measurement. On the basis of the thus estimated life of the sensor are automatically made the estimation of an exchange term limit and the warning of a need of preparations for a new sensor to a user, and so forth.

Taking by way of example the case where an ion-selective electrode is used as the sensor, the operation record parameter providing the index of the life may include one selected from the number of samples to be measured, a slope sensitivity, a response speed, the stability of potential, the resistance of electrode and a simultaneous reproducibility, or the plural combination thereof.

The parameter providing the index of the life can be stored in the memory of the analyzer body. On the other hand, the storage of this parameter in the non-volatile memory in the sensor makes the management of information accurate or easy since the sensor and information concerning that sensor have a one-to-one correspondence. The sensor is often subjected to temporary replacement for the maintenance of the analyzer or the like. In this case, the merit of physical coexistence of information and sensor is significant. Also, when seeing from the analyzer body side, it is not required that parameters used for the life estimation for all sensors be stored in the memory of the analyzer body. Therefore, a unitary or centralized data management becomes possible, thereby facilitating the processing. Further, the storage capacity can be saved. Of course, the parameter providing the index of the life can be stored in both the memory of the sensor and the memory of analyzer body so that one of the two memories can be used as a backup memory, thereby enhancing a safety against the loss of information.

Next, explanation will be made of a second additional operation or the optimization of a measuring sequence. The analyzer body operates so that an operation record parameter providing a index of the operating characteristic of the sensor acquired at the time of measurement or at the time of maintenance is properly stored into the non-volatile memory. In optimizing the measuring sequence, this operation record parameter is read from the non-volatile memory to analyze the tendency of change of the parameter value for the lapse of time. Thus, the present state of the sensor operating characteristic is grasped to correspondingly determine the optimum measuring sequence.

Taking by way of example the case where an ion-selective electrode is used as the sensor, the operation record parameter providing the index of the operating characteristic may include one selected from a response speed, the resistance of electrode, a slope sensitivity, the stability of potential, the number of measured sample and a simultaneous reproducibility, or the plural combination thereof. For example, when the response speed is sufficiently high, a high-speed measuring sequence is employed. When the response speed is deteriorated with use, a lower-speed measuring sequence is employed. By thus optimizing the sequence in accordance with the sensor characteristic, a measuring time is shortened to the limit of performance of the electrode, thereby making it possible to attain the maximum accuracy within a limited time.

Though the parameter providing the index of the operating characteristic of the sensor can also be stored in the memory 100 of the analyzer body, the storage of this parameter in the non-volatile memory of the sensor results in effects similar to those in the above-mentioned first operation, that is, the accuracy of information, the simplification of an information processing, the saving of the storage capacity of the analyzer body, the prevention of the loss of information, and so forth.

In connection with the operating record of the sensor, it is of course that the manufacturing condition of the sensor can be stored in addition to the operating record of the sensor. The manufacturing condition of the sensor includes the kind, type, manufacturer's serial number, lot number and manufacturing date of the sensor, a person in charge of manufacture, a manufacturing apparatus, the operating condition of the manufacturing apparatus, and so forth.

According to the present embodiment, an operating record parameter providing a index of the sensor characteristic such as the life or the operating characteristic of a sensor is stored in a non-volatile memory and is analyzed, thereby enabling the estimation of the life or the optimization of the measuring sequence. This results in the effects of the accuracy of information, the simplification of an information processing, the saving of the storage capacity of an analyzer body, the prevention of the loss of information, and so forth.

Figure 5:
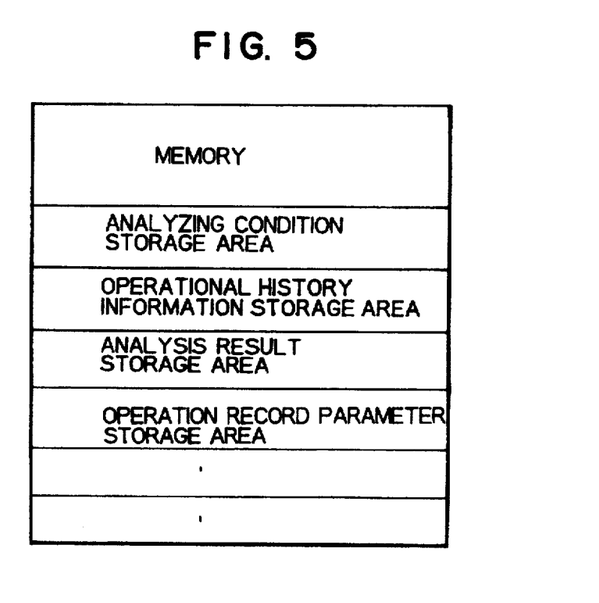
FIG. 5 shows storage areas of a memory.

It is preferable that analyzing condition and result of analysis of a sample and operation record parameter of a sensor are stored in the memory of the sensor together with the above-mentioned operational history information. Such a memory structure is shown in FIG. 5.

One example of a method of storing the result of analysis is as follows. Namely, with data for each sample being taken as one record and with a plurality of fields being defined in each record, data are stored in the respective fields of the record. The data to be stored includes a sample number, a sample name, a measurement item code, a measurement item name, a measured value, a correcting condition, a corrected value, a measuring date, a measuring apparatus, the result of operation, and so forth. All of the data can be acquired from the controller. The measured value can be obtained from the sensor directly. Each data can be distinguished in accordance with the position of a field.

By thus storing the results of analysis in not only the memory of the analyzer body but also the non-volatile memory of a sensor taking charge of the analysis, the following effects are provided. Namely, it is possible to back up the results of analysis. Also, even in the case where any fault in the sensor is confirmed later on, the judgement as to which of the results of analysis should be reexamined can be made readily by analyzing the results of analysis.

With the storage of the result of analysis in the non-volatile memory of the sensor, the transportability of data is improved. By carrying or delivering the sensor in a form removed from the analyzer body, as required, it is possible to easily transmit the result of analysis to a remote place. In this case, if a member including the non-volatile memory is formed as a part unit, as explained in conjunction with the second embodiment, the result of analysis can be transmitted more simply by carrying or delivering the unit in a form removed from the sensor.

Not only the results of analysis but also a measuring conditions can be stored in the non-volatile memory of the sensor. This construction provides an effect that even in the case where the use of the sensor under an unexpected measuring condition causes any troublesome result of analysis, it is possible to easily study the cause of the trouble and to easily make the judgement as to which of the results of analysis should be reexamined. As in the case of the result of analysis or measured value as mentioned above, the measuring condition can be stored in such a manner that a field for measuring condition is defined in each record and the measuring condition is stored in that field.

According to the present embodiment mentioned above, the reliability and transportability of data can be improved and the maintenance is facilitated.

[Embodiment 4]

Figure 6:
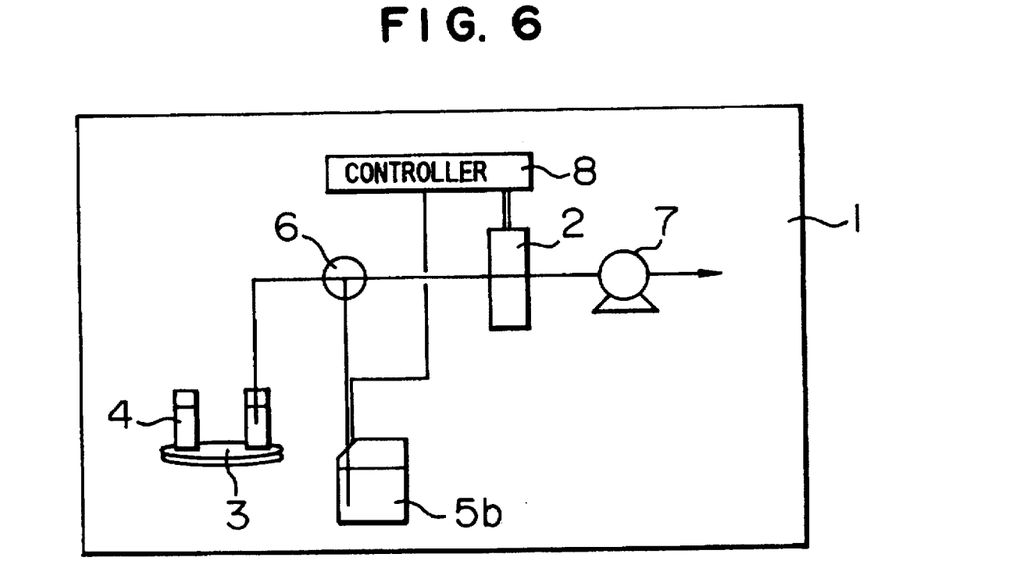
FIG. 6 is a diagram schematically showing the construction of an analyzer according to still another embodiment of the present invention.
Figure 7:
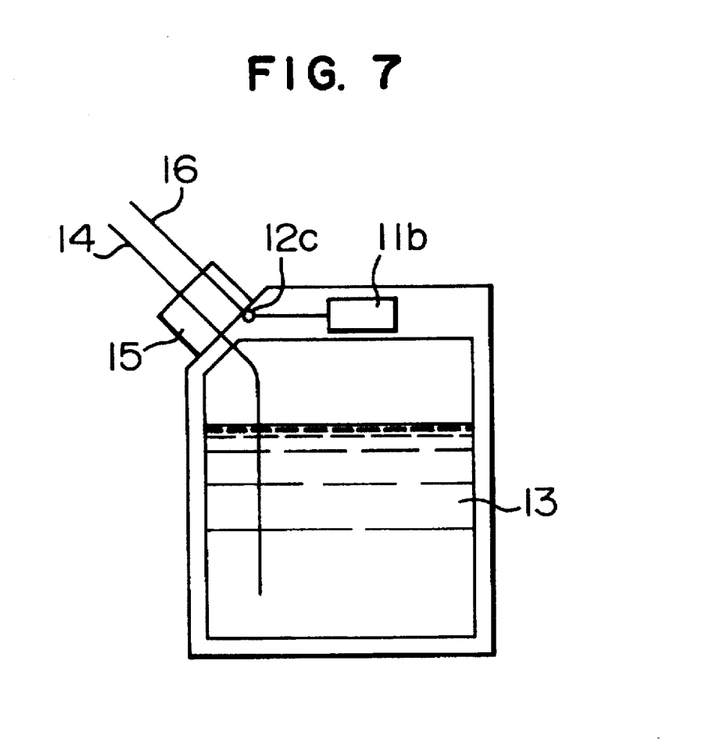
FIG. 7 is a diagram schematically showing the construction of an assembly of reagent vessel and memory in the embodiment shown in FIG. 6.

Next, a fourth embodiment of the present invention will be explained using FIGS. 6 and 7. FIG. 6 is a diagram schematically showing the construction of an analyzer of the present embodiment. The construction of the present embodiment is substantially similar to that of the first embodiment except a reagent vessel 5b. FIG. 7 is a diagram schematically showing the construction of the reagent vessel 5b. Reference numeral 13 denotes a reagent, numeral 11b a non-volatile memory, and numeral 12c a connector. A reagent tube 14, a cap 15 and a communication line 16 shown in FIG. 7 are constituent elements of not the reagent vessel 5b but an analyzer body 1.

The outline of operation will now be explained. The reagent vessel 5b is mounted on the analyzer body 1. If new information such as a newer analyzing condition than the analyzing condition inherently provided in the analyzer body 1 is stored in the non-volatile memory 11b included in the reagent vessel 5b, the controller 8 reads this new information through the connector 12c and replaces or extends the inherently provided information by the read new information, as required.

A sample in the sample vessel 4 is pipetted and diluted by the sampling mechanism 3. A part of the diluted sample and the reagent 13 in the reagent vessel 5b are selected by the electromagnetic valve 6 and are alternately supplied to the passage 9 in the sensor 2 by the solution feeding mechanism 7. A signal corresponding to the concentration of a specified component included in each of the diluted sample and the reagent 13 is outputted from the sensor 2 to the controller 8 by the action of the sensing member 10 provided in contact with the passage 9. The controller 8 determines the concentration of the specified component in the sample on the basis of the detection signal, the concentration of the specified component included in the reagent and the magnifying factor of dilution. The determined concentration of the specified component in the sample is displayed, outputted and stored. The above analyzing operation is controlled by the controller 8. As mentioned above, the operating condition is automatically replaced or extended in accordance with a new or corrected analyzing condition stored in the non-volatile memory 11b included in the reagent vessel 5b, as required.

Next, each element in the present embodiment will be explained in more detail. In general, a reagent is a consumable part. In order to facilitate the exchange of the spent reagent for a new reagent, the reagent vessel is easily detachable from the reagent tube 14, the cap 15 and the communication line 16 of the analyzer body.

The specification of the reagent may be changed according to circumstances. In order to cope with such a case, it may be preferable that the analyzing condition of the analyzer body is changed. In order to input such a large amount of unexpected new information to the analyzer body, the non-volatile memory 11b is incorporated in the reagent vessel 5b and the analyzer body is provided with a function of reading the contents of the non-volatile memory to replace or extend information inherently provided in the analyzer body, as required. A new reagent vessel to be subjected to a measurement under a new analyzing condition is delivered after a part or all of the new analyzing condition at the time of manufacture has been stored in a non-volatile memory of the new reagent vessel.

When the new reagent vessel is offered as an consumable part to a user and is mounted on an analyzer body, the analyzer body reads a part or all of the new analyzing condition to replace or extend information inherently provided in the analyzer body, thereby enabling a measurement under the new analyzing condition.

A more specific example will now be made in conjunction with the case where an internal standard reagent for ion-selective electrode is used as the reagent. As mentioned above, this internal standard reagent and a diluted sample are alternately supplied to the sensor and the concentration of the diluted sample is determined by the controller on the basis of the concentration of the internal standard reagent.

At the beginning, the concentration of an internal standard solution was used as a secondary standard. Namely, a measurement is made in such a manner that a plurality of primary standard solutions having a known concentration are arranged as a sample at a sampling section. The concentration of an internal standard reagent is determined by comparing the true concentration of the primary standard solution and the measurement value of concentration obtained as a measured value (on the basis of the concentration of the internal standard reagent). In the succeeding measurement of a sample having an unknown concentration, the concentration of the sample is calculated on the basis of the concentration of an internal standard reagent secondarily determined in the above-mentioned manner. However, in an analyzer developed later on, an internal standard solution is used as a primary standard. Namely, the concentration of a reagent is verified or qualified for each reagent vessel and the concentration of a sample is directly calculated on the basis of the verified value.

It is of course that the later-developed (or new-type) analyzer has employed the latter calculating method from the beginning. However, the present embodiment can cope with an old-type analyzer as follows. Namely, in the present embodiment, a new software for performing the changed new standardizing method and calculating method and the verified value of the concentration of the reagent are stored in the non-volatile memory incorporated in the new reagent vessel.

When the new reagent vessel is offered to a user and is mounted on the old-type analyzer, the analyzer body reads the new standardizing method and calculating method to replace a standardizing method and calculating method inherently provided in the analyzer body and further reads the verified value of the concentration of the reagent to use it for calculation. On the other hand, when the new reagent vessel is mounted on the new-type analyzer, the analyzer body reads the new standardizing method and calculating method but confirms that the read methods are the same as those inherently provided in the analyzer body. As a result, no displacement or extension of the standardizing method and calculating method is made. But, the verified reagent concentration value read by the analyzer body is used for calculation.

Thereby, the user can enjoy a merit that the measurement can be simplified. In updating the standardizing method and calculating method and transmitting the verified reagent concentration value, the minimum operation of mounting the new reagent vessel to the analyzer body is only needed for the user side and it is not required at all that the user be conscious of the updating of the standardizing method and calculating method and the transmission of the verified reagent concentration value. Also, only the mere change of the kinds of reagent vessels to be handled suffices on a supporting department side which supplies reagent vessels to users.

Though the foregoing explanation has been made taking the internal standard solution as one example, the reagent vessel is not limited to the internal standard solution. It is possible to similarly cope with reagent vessels of various external standard solutions disposed together with samples at the sampling mechanism. Also, though the foregoing explanation has been made the updating of the standardizing method and calculating method as an example of the new analyzing condition, the new analyzing condition is not limited to such an example. The optimum analyzing conditions corresponding to any improvement in performance or change in specification concerning reagents can be supplied to all types of analyzer bodies very simply in a manner similar to that mentioned above.

Further, though the foregoing explanation has been made taking the internal standard reagent for ion-selective electrode as an example of the reagent, it is of course that the present embodiment is also applicable to other reagents, for example, various luminometric reagents, colorimetric reagents, fluorimetric reagents, chemi-luminescent reagents, enzymatic reagents, immunometric reagents, or biochemical reagents. The analyzing conditions concerning these reagents may include, for example, the amount of use of reagent, the amount of use of sample, the magnifying factor of dilution of reagent, the magnifying factor of dilution of sample, buffer solution, pH, reaction temperature, reaction time, measurement time, measurement interval time, evaluating method (transmittance, absorbance, the intensity of fluorescence, the intensity of luminescence, the intensity of scattered light, current, voltage, or electrical resistance), evaluating condition (excitation wavelength, measuring wavelength, temperature, or pressure), evaluating mode (end-point assay method or rate assay method), and so forth. By storing such information in a non-volatile memory of a reagent vessel, as required, the information can be supplied to all types of analyzer bodies very simply.

In this connection, it is of course that the manufacturing condition of the reagent can be stored. The manufacturing condition of the reagent includes the kind, type, manufacturer's serial number, lot number and manufacturing date of the reagent, a person in charge of manufacture of the reagent, a manufacturing apparatus of the reagent, the operating condition of the manufacturing apparatus, and so forth.

According to the present embodiment mentioned above, even in the case where the improvement in performance or change in specification of a reagent is made so that an analyzing condition inherently provided in an analyzer body is to be replaced or extended by the optimum analyzing condition, the optimum analyzing condition can be inputted to the analyzer by merely mounting a reagent vessel to the analyzer body without needing any special operation.

[Embodiment 5]

Figure 8:
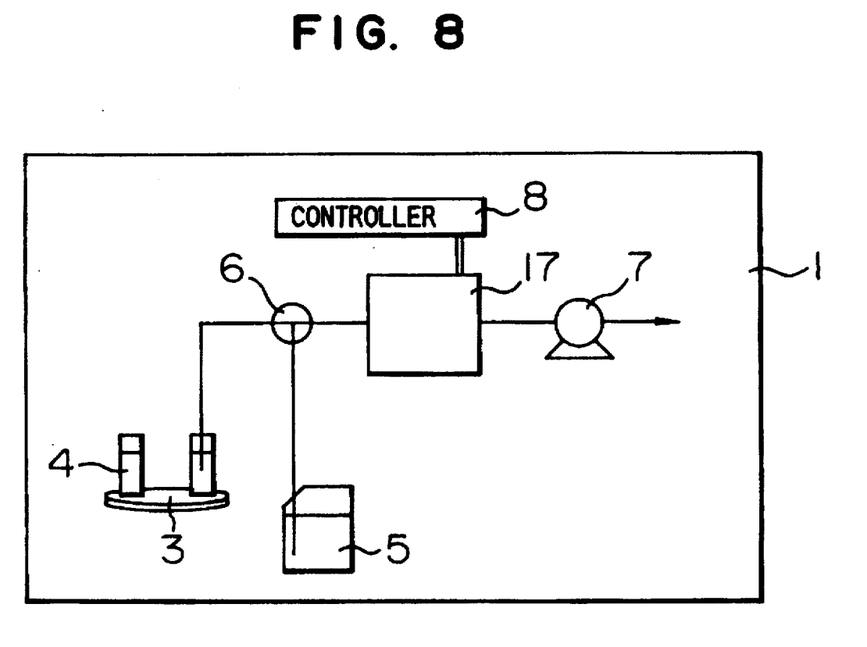
FIG. 8 is a diagram schematically showing the construction of an analyzer according to a further embodiment of the present invention.
Figure 9:
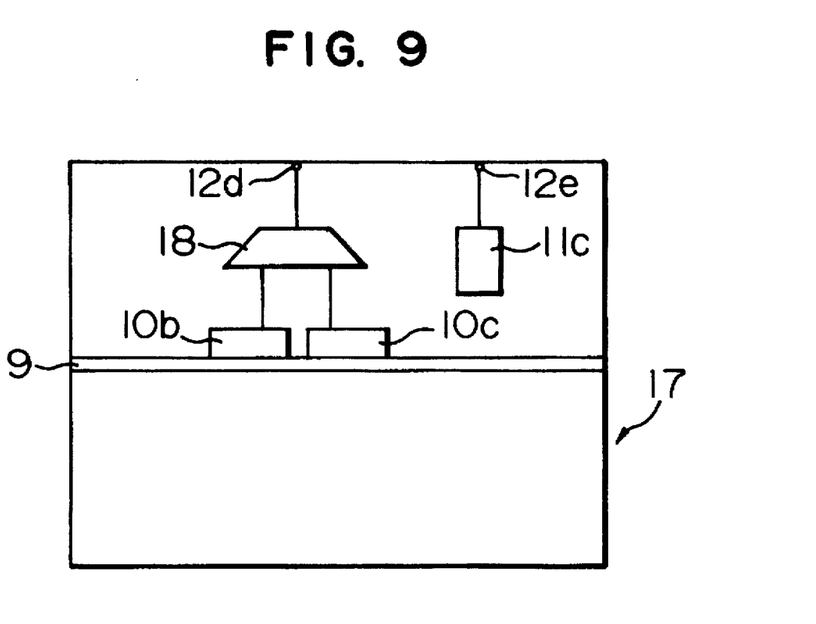
FIG. 9 is a diagram schematically showing the construction of a sensor-memory assembly in the embodiment shown in FIG. 8.

Next, a fifth embodiment of the present invention will be explained using FIGS. 8 and 9. FIG. 8 is a diagram schematically showing the construction of an analyzer of the present embodiment. The operation of the present embodiment is substantially similar to that of the first embodiment, excepting that a multisensor 17 is used as a sensor. FIG. 9 is a diagram schematicaly showing the construction of the multisensor 17. Reference numeral 9 denotes a passage, numerals 10b and 10c sensing members, numerals 12d and 12e connectors, and numeral 18 a multiplexer. As apparent from FIG. 9, the multisensor 17 is substantially equivalent to the sensor 2 in the first embodiment, excepting that the multisensor 17 includes a plurality of sensing members (for example, a plurality of ion sensors) and the multiplexer 18 is used.

The outline of operation will now be explained. The multisensor 17 is mounted on the analyzer body 1. In the case where new information such as a newer analyzing condition than the analyzing condition inherently provided in the analyzer body 1 is stored in the non-volatile memory 11c included in the multisensor 17, the controller 8 reads this new information through the connector 12e and replaces or extends the inherently provided information by the read new information, as required.

A sample in the sample vessel 4 is partially extracted and diluted by the sampling mechanism 3. A part of the diluted sample and the reagent 13 in the reagent vessel 5 are selected by the electromagnetic valve 6 and are alternately supplied to the passage 9 in the multisensor 17 by the solution feeding mechanism 7. The sensing members 10b and 10c provided in contact with the passage 9 output signals corresponding to the concentrations of first and second specified components included in each of the diluted sample and the reagent. The multiplexer 18 successively selects one of these signals and outputs it to the connector 12d. On the basis of those signals, the concentrations of the first and second specified components included in the reagent and the magnifying factor of dilution, the controller 8 determines the concentrations of the first and second specified components in the sample. The determined concentration is displayed, outputted and stored. The above analyzing operation is controlled by the controller 8.

In the present embodiment, the foregoing operation provides effects similar to those in the first embodiment. Further, the following effects peculiar to the present embodiment can be provided. In the present embodiment, the number of measurement items can be increased by increasing the number of sensing members which form the multisensor 17. Also, the precision of measurement of a specified component can be improved, for example, by measuring an interfering component by use of the increased number of measurement items and making the correction for the interference by use of a selectively coefficient for the specified component. Even in the case where information of a new analysis procedure, analyzing method, data processing method is to be inputted to an old-type analyzer to make such a large change in specification, an operating condition inherently provided in the analyzer body is automatically replaced or extended by the new or corrected analyzing condition, as required, by storing the above information in a non-volatile memory 11c incorporated in a multisensor 17. Namely, the present embodiment can flexibly cope with the increase in number of measurement items in an analyzing system using a multisensor and the improvement in precision of measurement associated therewith.

[Embodiment 6]

Figure 10:
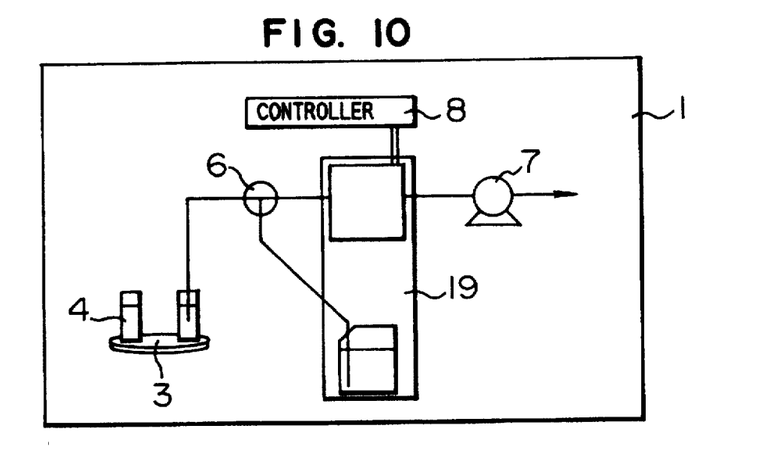
FIG. 10 is a diagram schematically showing the construction of an analyzer according to a still further embodiment of the present invention.

Next, a sixth embodiment of the present invention will be explained using FIG. 10. FIG. 10 is a diagram schematically showing the construction of an analyzing system according to the present embodiment. The analyzing system of the present embodiment is substantially similar to those of the fifth and fourth embodiments, excepting that a multisensor in the fifth embodiment and a reagent vessel in the fourth embodiment are incorporated in the same package or an analyzing package 19. Though the analyzing package 19 has a basic form in which that the multisensor shown in FIG. 9 and the reagent vessel shown in FIG. 7 are incorporated in the same package, the non-volatile memory and the connector are put to not a double use but a common use.

The operation of the present invention is substantially similar to those of the fifth and fourth embodiments. The present embodiment provides not only effects similar to those in the fifth and fourth embodiments but also an effect that the unification of consumable or wearing replaceable parts in one analyzing package saves a labor of parts exchange by a user, thereby improving the convenience or easiness of use.

[Embodiment 7]

Figure 11:
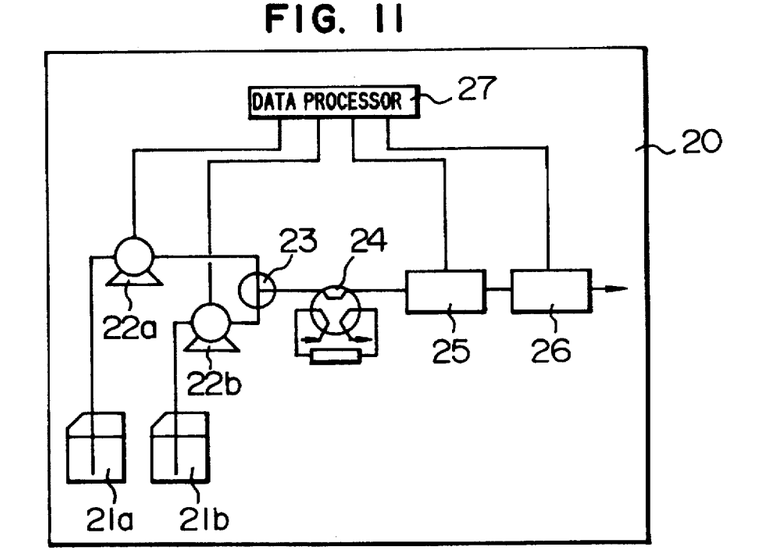
FIG. 11 is a diagram schematically showing the construction of an analyzer according to a furthermore embodiment of the present invention.
Figure 12:
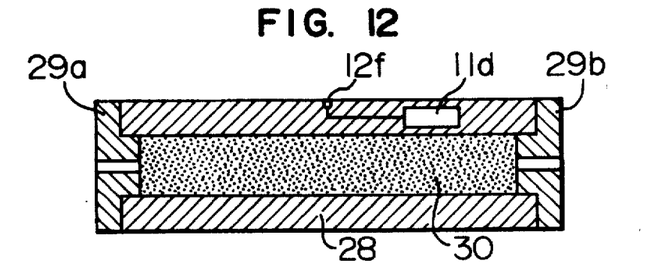
FIG. 12 is a view schematically showing the construction of a column-memory assembly in the embodiment shown in FIG. 11.

Next, a seventh embodiment of the present invention will be explained using FIGS. 11 and 12. FIG. 11 is a diagram schematically showing the construction of an analyzing system according to the present embodiment. Reference numeral 20 denotes a liquid chromatograph body, numerals 21a and 21b eluents, numerals 22a and 22b pumps, numeral 23 a mixer, numeral 24 an injector, numeral 25 a column, numeral 26 a detector, and numeral 27 a data processor. Since the column 25 is a replaceable part which is consumed or worn, it is attachable to and detachable from the liquid chromatograph body 20. FIG. 12 schematically shows a cross section of the column 25. Reference numeral 28 denotes a column body, numerals 29a and 29b end fittings, numeral 30 a filler, numeral 11d a non-volatile memory, and numeral 12f a connector.

The outline of the operation of the present embodiment will now be explained. The eluents 21a and 21b are pressed by the pumps 22a and 22b and are mixed by the mixer 23 at a proper mixing ratio. The mixed elutent is introduced into the injector 24. A sample to be analyzed is injected by the injector 24 into the flow of the mixed eluent and is separated by the column 25 into individual components which are in turn detected quantitatively by the detector 26. The detector 26 may be, for example, an ultraviolet-ray absorptiometric detector. The above operation is controlled by the data processor 27.

In the case where new information such as a newer analyzing condition than the analyzing condition inherently provided in the analysis data processor 27 is stored in the non-volatile memory 11d included in the column 25, the data processor 27 reads this new information through the connector 12f and replaces or extends the inherently provided information by the read new information, as required. Accordingly, even in the case where the improvement in performance or change in specification of a column is made, a large amount of new information of new analyzing condition or the like associated therewith can be inputted to the liquid chromatograph body by simple means. An example of the new analyzing condition concerning the column includes the mixing ratio of eluents, the temporary change of mixing ratio, the pressure of pump, the flow rate of eluent, the temperature of column, the composition of eluent, the retention time of separated component, the number of theoretical plates of column, and so forth.

Though the foregoing explanation has been made taking by way of example the case where the non-volatile memory is incorporated in the column, it is of course that a similar mechanism can also be provided to a member reserving the eluent in order that the liquid chromatograph body is informed of the optimum analyzing condition adapted to the composition of the eluent.

According to the present embodiment mentioned above, even in the case where the improvement in performance or change in specification of a column or eluent is made so that an analyzing condition inherently provided in a liquid chromatography body is to be replaced or extended by the optimum analyzing condition, the optimum analyzing condition can be inputted to the liquid chromatography by the minimum operation of mounting a column or an eluent reserving member to the liquid chromatograph body.

Though the above has been explained taking the liquid chromatograph as one example, the present invention is applicable to an analyzing system utilizing gas chromatograph, supercritical fluid chromatograph or any one of other various chromatographs with a similar effect. It is of course that the present invention is also applicable to various separative analysis apparatuses other than the chromatography, for example, an electrophoresis apparatus, a capillary electrophoresis apparatus, or an analyzing system for separatively analyzing a biomaterial such as protein, nucleic acid, sugar, lipid or a complex thereof by use of the principle of electrophoresis or capillary electrophoresis.

Though reference is not made explicitly in the foregoing explanation, the present invention is not limited to the scope of the disclosed embodiments and is generally applicable to an analyzing system based on any principle.

A sensor, to which the present invention is applicable, is not limited to the sensors explained in conjunction with the embodiments. The present invention can be applied to various kinds of sensors including a gas sensor for measuring carbon dioxide gas, oxygen gas, ammonia gas, amine, acetone, narcotic gas, alcohol or the like, an enzyme sensor for measuring glucose, urea or the like in a blood or urine by use of an enzyme, an immunosensor for measuring hormone, pathogenic fungi, cancer marker or the like in a blood or urine by use of an anitigen-antibody reaction, a protein sensor for uric protein meter, an occult blood sensor for uric occult blood detector or colonic cancer detector, an urobilinogen sensor for uric urobilinogen meter, an ultrasonic transducer for ultrasonic diagnosis apparatus, a potential sensor used in an electrocardiograph, electromynograph, electroencephalograph or the like, a pressure sensor used in a sphygmomanometer, identation tonometer, weight meter or the like, and a temperature sensor used in a clinical thermometer, tympanum thermometer or the like.

According to the present invention as mentioned above, in an analyzing system using a consumable replaceable part such as a sensor or reagent bearing a part of an analyzing function, a large amount of information inclusive of a new analyzing condition concerning the replaceable part can be inputted to an analyzer simply without requiring any special means.

We claim:

1. An analyzer comprising:

an analyzer body including means for holding a sample, means for reading an analyzing condition from memory means, means for performing analysis of said sample on the basis of the read analyzing condition, and means for outputting a result of said analysis of said sample; and an assembly detachably mounted on said analyzer body, said assembly including a passage through which said sample passes during said analysis of said sample, sensing means having a characteristic of inherently defining an analyzing condition of said sample, said sensing means being in contact with said passage, and said memory means, said memory means being for holding the analyzing condition defined by said sensing means.

2. An analyzer according to claim 1, wherein said assembly further includes second memory means for holding the result of said analysis of said sample, and said analyzer body further includes means for writing the result of said analysis of said sample into said second memory means.

3. An analyzer according to claim 1, wherein said assembly further includes third memory means for holding operational history information of use of said sensing means, and said analyzer body further includes means for writing the operational history information of use of said sensing means into said third memory means.

4. An analyzer according to claim 1, wherein said memory means includes a non-volatile memory.

5. An analyzer according to claim 1, wherein said memory means is attachable to and detachable from said sensing means, and said sensing means is attachable to and detachable from said analyzer body.

6. An analyzer body on which an assembly is to be detachably mounted, said assembly including a passage through which a sample passes during analysis of said sample, sensing means having a characteristic of inherently defining an analyzing condition of said sample, said sensing means being in contact with said passage, and memory means for holding the analyzing condition defined by said sensing means, the analyzer body comprising:

means for holding said sample;

means for reading the analyzing condition from said memory means;

means for performing said analysis of said sample on the basis of the read analyzing condition; and means for outputting a result of said analysis of said sample.

7. An analyzer body according to claim 6, wherein said assembly further includes second memory means; and wherein said analyzer body further comprises means for writing said result of said analysis of said sample into said second memory means.

8. An analyzer body according to claim 6, wherein said assembly further includes third memory means; and wherein said analyzer body further comprises means for writing operational history information of use of said sensing means into said third memory means.

9. An assembly which is to be detachably mounted on an analyzer body, said analyzer body including means for holding a sample, means for reading an analyzing condition from memory means, means for performing analysis of said sample on the basis of the read analyzing condition, and means for outputting a result of said analysis of said sample, the assembly comprising:

a passage through which said sample passes during said analysis of said sample;

sensing means having a characteristic of inherently defining an analyzing condition of said sample, said sensing means being in contact with said passage; and said memory means, said memory means being for holding the analyzing condition defined by said sensing means.

10. An assembly according to claim 9, further comprising second memory means for holding said result of said analysis of said sample.

11. An assembly according to claim 9, further comprising third memory means for holding operational history information of use of said sensing means.

12. An assembly according to claim 9, wherein said memory means includes a non-volatile memory.

13. An assembly according to claim 10, wherein said second memory means includes a non-volatile memory.

14. An assembly according to claim 11, wherein said third memory means includes a non-volatile memory.

15. An assembly according to claim 9, wherein said memory means is attachable to and detachable from said sensing means, and said sensing means is attachable to and detachable from said analyzer body.

16. An assembly which is to be detachably mounted on an analyzer body, said analyzer body including means for holding a sample, means for reading an analyzing condition from memory means, means for performing analysis of said sample on the basis of the read analyzing condition, and means for outputting a result of said analysis of said sample, the assembly comprising:

a sensing means package including a passage through which said sample passes during said analysis of said sample, sensing means having a characteristic of inherently defining an analyzing condition of said sample, said sensing means being in contact with said passage, and first connecting means for detachably connecting said sensing means package to said analyzer body;

a memory unit including said memory means, said memory means being for holding said analyzing condition defined by said sensing means, and second connecting means for connecting said memory means to said reading means of said analyzer body; and third connecting means for detachably connecting said sensing means package and said memory unit to each other.

17. An assembly according to claim 16, wherein said memory unit further includes second memory means for holding said result of said analysis of said sample.

18. An assembly according to claim 16, wherein said memory unit further includes third memory means for holding operational history information of use of said sensing means.

19. An assembly according to claim 16, wherein said memory means includes a non-volatile memory.

20. An assembly according to claim 17, wherein said second memory means includes a non-volatile memory.

21. An assembly according to claim 18, wherein said third memory means includes a non-volatile memory.

22. A sensing means package which is to be detachably mounted on an analyzer body, said analyzer body including means for holding a sample, means for reading an analyzing condition from memory means, means for performing analysis of said sample on the basis of the read analyzing condition, and means for outputting a result of said analysis of said sample, the sensing means package comprising:

a passage through which said sample passes during said analysis of said sample;

sensing means having a characteristic of inherently defining an analyzing condition of said sample, said sensing means being in contact with said passage;

first connecting means for detachably connecting said sensing means package to said analyzer body; and mounting means on which a memory unit is to be detachably mounted, said memory unit including said memory means, said memory means being for holding said analyzing condition defined by said sensing means, and second connecting means for connecting said memory means to said reading means of said analyzer body.

23. A memory unit which is to be detachably mounted on an analyzer body, said analyzer body including means for holding a sample, means for reading an analyzing condition from memory means, means for performing analysis of said sample on the basis of the read analyzing condition, and means for outputting a result of said analysis of said sample, the memory unit comprising:

said memory means, said memory means being for holding said analyzing condition;

first connecting means for connecting said memory means to said reading means of said analyzer body; and mounting means for detachably mounting the memory unit on a sensing means package, said sensing means package including a passage through which said sample passes during said analysis of said sample, sensing means having a characteristic of inherently defining an analyzing condition of said sample, said memory means being for holding said analyzing condition defined by said sensing means, said sensing means being in contact with said passage, and second connecting means for detachably connecting said sensing means package to said analyzer body.

24. A memory unit according to claim 23, further comprising second memory means for holding said result of said analysis of said sample.

25. A memory unit according to claim 23, further comprising third memory means for holding operational history information of use of said sensing means.

26. A memory unit according to claim 23, wherein said memory means includes a non-volatile memory.

27. A memory unit according to claim 24, wherein said second memory means includes a non-volatile memory.

28. A memory unit according to claim 25, wherein said third memory means includes a non-volatile memory.

29. An automatic blood analyzer comprising:

an analyzer body including means for holding a sample, means for reading an analyzing condition from a non-volatile memory, means for performing analysis of said sample on the basis of the read analyzing condition, and means for outputting a result of said analysis of said sample; and an assembly detachably mounted on said analyzer body, said assembly including a passage through which said sample passes during said analysis of said sample, an electrode having a characteristic of inherently defining an analyzing condition of said sample, said electrode being in contact with said passage, and said non-volatile memory, said non-volatile memory being for holding the analyzing condition defined by said electrode.

30. An analyzer comprising:

an analyzer body including means for holding a sample, means for performing analysis of said sample on the basis of a predetermined analyzing condition, means for outputting a result of said analysis of said sample, and means for writing the result of said analysis of said sample and/or operational history information of use of sensing means into memory means; and an assembly detachably mounted on said analyzer body, said assembly including a passage through which said sample passes during said analysis of said sample, said sensing means, said sensing means having a characteristic of inherently defining an analyzing condition of said sample and being in contact with said passage, and said memory means, said memory means being for holding said result of said analysis of said sample and/or said operational history information of use of said sensing means.

31. An analyzer comprising:

an analyzer body including means for holding a sample, means for reading software from memory means, the software describing a procedure for performing analysis of the sample, means for performing the analysis of the sample on the basis of the procedure described by the software, and means for outputting a result of the analysis of the sample; and an assembly detachably mounted on the analyzer body, the assembly including an element having a characteristic of inherently defining the procedure for performing the analysis of the sample described by the software, and the memory means.

32. An analyzer according to claim 31, wherein the element and the memory means are incorporated in the assembly such that the memory means is not detachable from the assembly.

33. An analyzer according to claim 31, wherein the memory means is attachable to and detachable from the element, and the element is attachable to and detachable from the analyzer body.

34. An analyzer comprising:

an analyzer body including means for holding a sample, means for reading software from memory means, the software describing a procedure for performing analysis of the sample, means for performing the analysis of the sample on the basis of the procedure described by the software, and means for outputting a result of the analysis of the sample; and an assembly detachably mounted on the analyzer body, the assembly including an element having a characteristic of inherently defining the procedure for performing the analysis of the sample described by the software, the memory means, and a circuit for carrying out serial communication between the memory means and the analyzer body.

35. An analyzer according to claim 34, wherein the element and the memory means are incorporated in the assembly such that the memory means is not detachable from the assembly.

36. An analyzer according to claim 34, wherein the memory means is attachable to and detachable from the element, and the element is attachable to and detachable from the analyzer body.

37. An analyzer according to claim 1, wherein said sensing means includes an ion-selective electrode.

38. An analyzer body according to claim 6, wherein said sensing means includes an ion-selective electrode.

39. An assembly according to claim 9, wherein said sensing means includes an ion-selective electrode.

40. An assembly according to claim 16, wherein said sensing means includes an ion-selective electrode.

41. A sensing means package according to claim 22, wherein said sensing means includes an ion-selective electrode.

42. A memory unit according to claim 23, wherein said sensing means includes an ion-selective electrode.

43. An automatic blood analyzer according to claim 29, wherein said electrode is an ion-selective electrode.

44. An analyzer according to claim 30, wherein said sensing means includes an ion-selective electrode.

45. An analyzer according to claim 31, wherein the assembly further includes a passage through which the sample passes during the analysis of the sample; and wherein the element is in contact with the passage.

46. An analyzer according to claim 31, wherein the element includes an ion-selective electrode.

47. An analyzer according to claim 34, wherein the assembly further includes a passage through which the sample passes during the analysis of the sample; and wherein the element is in contact with the passage.

48. An analyzer according to claim 34, wherein the element includes an ion-selective electrode.

* * * * *